US00PP33240P2

(12) United States Plant Patent
van Steijn

(10) Patent No.: US PP33,240 P2
(45) Date of Patent: Jul. 6, 2021

(54) ***LIMONIUM* PLANT NAMED 'STE10'**

(50) Latin Name: *Limonium gmelinii*
Varietal Denomination: STE10

(71) Applicant: Petrus Theodorus van Steijn, Voorhout (NL)

(72) Inventor: Petrus Theodorus van Steijn, Voorhout (NL)

( * ) Notice: Subject to any disclaimer, the term of this patent is extended or adjusted under 35 U.S.C. 154(b) by 0 days.

(21) Appl. No.: 17/031,890

(22) Filed: Sep. 24, 2020

(30) Foreign Application Priority Data

Apr. 21, 2020 (QZ) ..... PBR 2020/1049

(51) Int. Cl.
*A01H 5/02* (2018.01)

(52) U.S. Cl.
USPC ..... Plt./339

(58) Field of Classification Search
USPC ..... Plt./339
See application file for complete search history.

*Primary Examiner* — Annette H Para
(74) *Attorney, Agent, or Firm* — Penny J. Aguirre

(57) ABSTRACT

A new cultivar of *Limonium* plant named 'STE10' that is characterized by its compact plant size, its flowers that are purple in color, its floriferous blooming habit, and its drought resistance.

2 Drawing Sheets

Botanical classification: *Limonium gmelinii.*
Cultivar designation: 'STE10'.

CROSS-REFERENCE TO A RELATED APPLICATION

This application claims priority to European Community Plant Variety Office (CPVO) Plant Breeder's Rights Application No. 2020/1049 filed on Apr. 21, 2020, under 35 U.S.C. 119(f), the entire contents of which is incorporated by reference herein.

BACKGROUND OF THE INVENTION

The present invention relates to a new and distinct cultivar of *Limonium*, botanically known as a *Limonium gmelinii* 'STE10', and is hereinafter referred to by its cultivar name 'STE10'. 'STE10' is a new cultivar of Siberian statice, a hardy perennial grown for landscape use.

The new cultivar was discovered as a chance seedling in a trial field by the Inventor in Voorhout, The Netherlands in July of 2012. The trial field contained proprietary *Limonium* seedlings from the Inventor's breeding program. The parentage of 'STE10' is therefore unknown.

Asexual propagation of the new cultivar was first accomplished under the direction of the Inventor by tissue culture initiated from meristem tissue in July of 2012 in Voorhout, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'STE10' as a new and unique cultivar of *Limonium.*

1. 'STE10' exhibits a compact plant size.
2. 'STE10' exhibits flowers that are purple in color.
3. 'STE10' exhibits a floriferous blooming habit.
4. 'STE10' exhibits drought resistance.

There are no known cultivars of *Limonium gmelinii* known to the Inventor; only seed strains such as MISTY BLUE (not patented). 'STE10' can be most closely compared to typical plants of *Limonium gmelinii* and *Limonium gmelinii* ssp. *hungaricum*. Typical plants of *Limonium gmelinii* and seed strains including MISTY BLUE are similar to 'STE10' in having sepals that are dry and papery in texture and inflorescences that make excellent cut flowers, but differ from 'STE10' in having a taller plant height, flowering stems that are thicker in diameter and less fine in texture and flowers that are smoky blue in color. Typical plants of *Limonium gmelinii* ssp. *hungaricum* are similar to 'STE10' in having funnel-shaped flowers and inflorescences that make excellent cut flowers, but differ from 'STE10' in having less flowers per inflorescence, flowering stems that are thicker in diameter and are less dense and less fine in texture and flowers that are lilac blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp, Youtube, Concept plants (all three by the Inventor's representative), Hortweek, Suttons Company, CouponX00, Garden for Pleasure, The English Garden Company, Living With Nature, Milled, and Pinterest.

BRIEF DESCRIPTION OF THE DRAWINGS

The accompanying colored photograph illustrates the overall appearance and distinct characteristics of the new *Limonium*. The photograph was taken of a plant 1 year in age as grown outdoors in a 17-cm container in Voorhout, The Netherlands.

The photograph in FIG. 1 provides a side view of the plant of 'STE10' in bloom.

Figure 1:
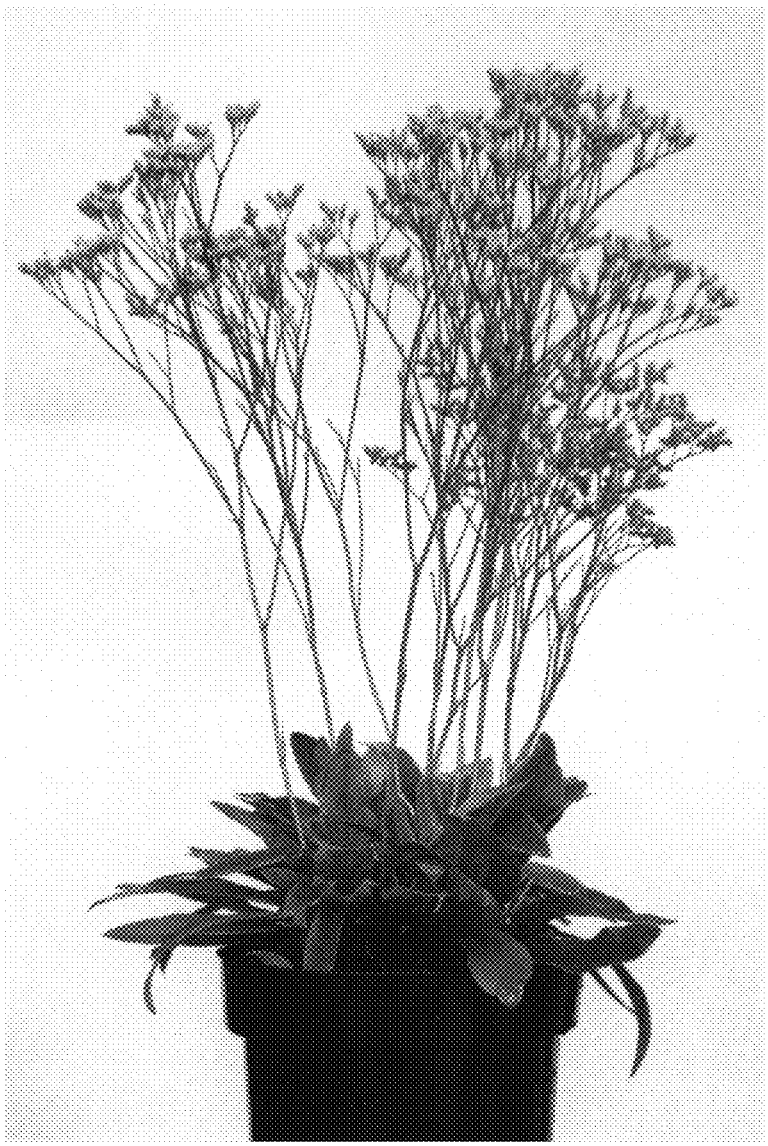
Figure 2:
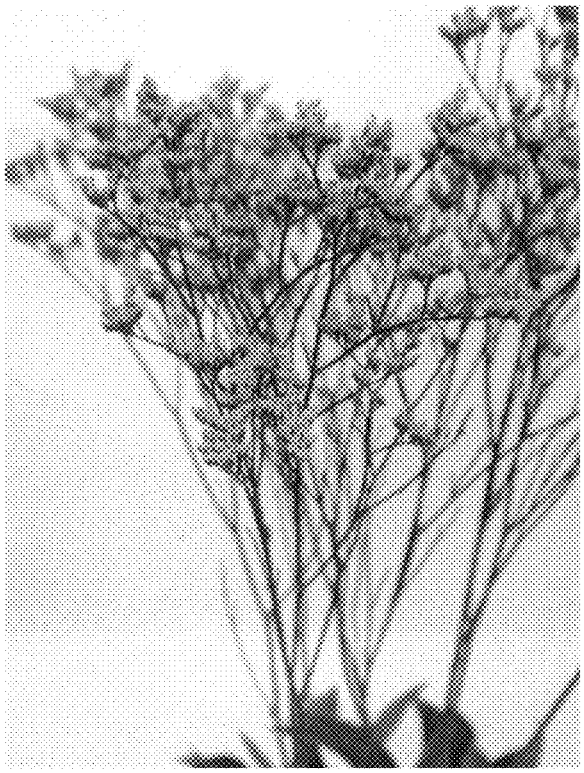

The photograph in FIG. 2 provides a close up of the inflorescences of 'STE10'.

Figure 3:
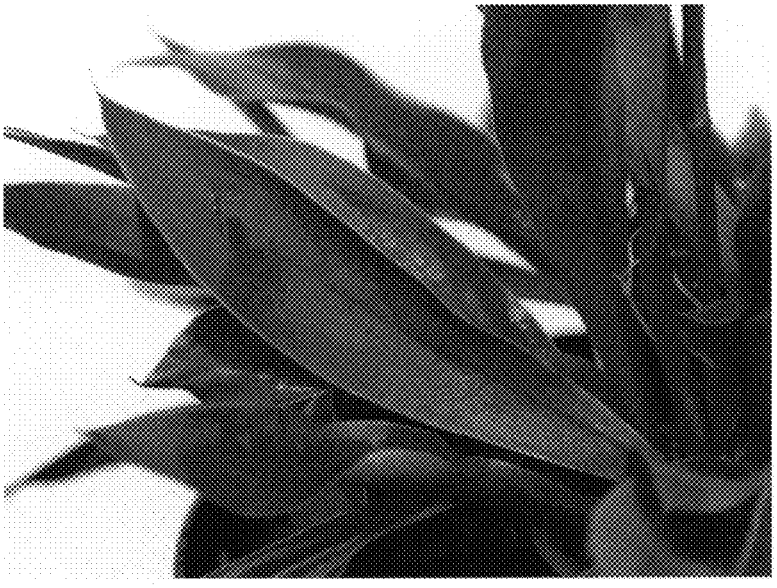

The photograph in FIG. 3 provides a close up of the foliage of 'STE10'.

The colors in the photograph are as close as possible with the digital photography techniques available, the color values cited in the detailed botanical description accurately describe the colors of the new *Limonium*.

DETAILED BOTANICAL DESCRIPTION OF THE PLANT

The following is a detailed description of 1-year-old plants of the new cultivar as grown outdoors in 17-cm containers in Voorhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to late summer in The Netherlands.

*Plant type*.—Herbaceous perennial.

*Plant habit*.—Upright and broadly spreading.

*Height and spread*.—An average of 11.5 cm in height (soil level to top of foliar plane), An average of 46.5 cm in height (soil level to top of floral plane), 35.3 cm in spread.

*Hardiness*.—At least in U.S.D.A. Zones 5a to 9b.

*Diseases and pests*.—No susceptibility or resistance to pests or diseases has been observed.

*Environmental stresses*.—Drought resistant.

*Root description*.—Fibrous roots on woody rootstalks.

*Propagation*.—Tissue culture.

*Root development*.—An average of 4 weeks for root initiation, 5 to 6 weeks to produce a young plant from a rooted small plant from tissue culture.

*Growth rate*.—Moderate to high.

Stem description (peduncle, flowering stem):

*Shape*.—Round.

*Stem color*.—137B to 137C, sunny side slightly darker 137A.

*Stem size*.—An average of 2.5 mm in diameter and 45.1 cm in length.

*Stem strength*.—Strong.

*Stem aspect*.—Average of 80° (varying between 70° and 90°).

*Stem surface*.—Slightly glossy, glabrous.

*Stem number*.—Average of 7 flowering stems.

*Branching habit*.—Flowering stems emerge from basal rosette.

Foliage description:

*Leaf shape*.—Oblanceolate to obovate.

*Leaf division*.—Simple.

*Leaf base*.—Sheathing.

*Sheath*.—Average of 1.8 cm in length, 3 mm in width, 155D in color.

*Leaf apex*.—Mucronate.

*Leaf venation*.—Pinnate, upper surface 137B, lower surface 146B.

*Leaf margins*.—Entire, slightly undulate.

*Leaf attachment*.—Sessile.

*Leaf arrangement*.—Alternate in basal rosettes.

*Leaf lobes*.—Lobed, an average of 7 lobes, shallow in depth, divergent.

*Leaf surface*.—Both surfaces smooth and glabrous, non-rugose, upper surface very slightly glossy, lower surface matte.

*Leaf color*.—Young upper surface 138A, young lower surface 144A, mature upper surface NN137A, mature lower surface 147B.

*Leaf size*.—An average of 13.5 cm in length and 3.1 cm in width.

*Leaf aspect*.—Flat to slightly carinate.

*Leaf quantity*.—An average of 7 (varying between 6 and 8) per basal rosette.

*Petioles*.—None.

*Stipules*.—None.

Flower description:

*Inflorescence type*.—Numerous small bell-shaped flowers arranged on panicles on peduncles emerging from a basal rosette.

*Cut flowers*.—Suitable as cut flowers, average of 10 stems harvested per year.

*Inflorescence size*.—An average of 28.6 cm in height and 16.9 cm in diameter.

*Inflorescence number*.—An average of 7.

*Flower fragrance*.—Faint, sweet and pleasant.

*Flower quantity*.—Average of 1,000 flowers per inflorescence, 7,500 per plant.

*Flower lastingness*.—Average of four weeks, persistent.

*Flower buds*.—Oblong in shape, an average of 4 mm in length and 1.5 mm in diameter, color; top of bud 85C, N82C to N82D, smooth, glabrous and very slightly glossy.

*Flower type*.—Rotate, single, consisting of one whorl of petals and one whorl of sepals.

*Flower aspect*.—Upright to very slightly outward.

*Flower size*.—Average of 3 mm in height and diameter, 7 mm in depth.

*Calyx*.—Rotate, 2.5 mm in length and 1.2 mm in diameter.

*Sepals*.—Average of 5, average of 4 mm in length, 0.75 mm in width, tubular in shape, broadly acute tip, 87.5% of base fused into tube, free tips with entire margins, both surfaces smooth, glabrous, very slightly glossy and slightly papery, color; when opening and fully open upper and lower surface 157C, slightly tinged 85D at the top, fading to 145C.

*Petals*.—Rotate in arrangement, average of 5, average of 4 mm in length, 1.75 mm in width, obovate to slightly concave in shape, obtuse tip, acuminate base, entire margins, both surfaces smooth, glabrous and matte, color; when opening upper surface N82C, main veins N81B to N81C, when opening lower surface and fully open upper and lower surface N82C, both surfaces fading to 95C.

*Floral bracts*.—At the base of each calyx there is a single bract, ovate in shape, acute tip, cuneate base, average of 2 mm in length, 1.25 mm in width, surfaces are smooth and glabrous, upper surface slightly glossy, lower surface matte, entire margins, colors; both surfaces 143C, margins 157A.

*Pedicels*.—None, individual flowers sessile to secondary peduncles.

Reproductive organs:

*Gynoecium*.—Pistils; 5, 0.3 mm in length, 0.1 mm in diameter, stigma; pointed in shape, N155A in color, style; an average of 4.7 mm in length and N155A in color, ovary; 144B in color.

*Androecium*.—Stamens; 5, anthers; dorsifixed, oblong in shape, 0.3 mm in length, 0.2 mm in width, color; 186C, margins 156D, filament; 6 mm in length and NN155D in color, pollen; moderate in quantity and 159D in color.

*Seed/fruit*.—No fruit or seeds were observed to date.

It is claimed:

1. A new and distinct cultivar of *Limonium* plant named 'STE10' as herein illustrated and described.

* * * * *